US012774262B2

(12) United States Patent
Dambrin

(10) Patent No.: US 12,774,262 B2
(45) Date of Patent: Oct. 27, 2026

(54) PROCESS FOR PREPARING FRAMBIONE

(71) Applicant: SPECIALTY OPERATIONS FRANCE, Lyons (FR)

(72) Inventor: Valéry Dambrin, Irigny (FR)

(73) Assignee: SPECIALTY OPERATIONS FRANCE, Lyons (FR)

( * ) Notice: Subject to any disclaimer, the term of this patent is extended or adjusted under 35 U.S.C. 154(b) by 649 days.

(21) Appl. No.: 18/252,823

(22) PCT Filed: Dec. 1, 2021

(86) PCT No.: PCT/EP2021/083815
§ 371 (c)(1),
(2) Date: May 12, 2023

(87) PCT Pub. No.: WO2022/117670
PCT Pub. Date: Jun. 9, 2022

(65) Prior Publication Data

US 2023/0416182 A1 Dec. 28, 2023

(30) Foreign Application Priority Data

Dec. 1, 2020 (FR) ...................................... 2012448

(51) Int. Cl.
*C07C 45/62* (2006.01)
*A23L 27/20* (2016.01)
*C07C 45/39* (2006.01)
*C07C 45/74* (2006.01)
*C07C 51/353* (2006.01)

(52) U.S. Cl.
CPC ............ *C07C 45/62* (2013.01); *A23L 27/204* (2016.08); *C07C 45/39* (2013.01); *C07C 45/74* (2013.01); *C07C 51/353* (2013.01)

(58) Field of Classification Search
USPC ........................................................ 568/319
See application file for complete search history.

(56) References Cited

U.S. PATENT DOCUMENTS

| | | | |
|---|---|---|---|
| 5,219,745 | A | 6/1993 | Anton et al. |
| 5,430,183 | A | 7/1995 | Nobel |
| 6,753,441 | B1 | 6/2004 | Jouve et al. |
| 2011/0009664 | A1 | 1/2011 | Heinisch et al. |
| 2011/0257439 | A1 | 10/2011 | Dutta et al. |
| 2011/0306802 | A1 | 12/2011 | Maliverney et al. |
| 2013/0232852 | A1 | 9/2013 | Peterson et al. |
| 2015/0183702 | A1 | 7/2015 | Garel |
| 2016/0297735 | A1 | 10/2016 | Garel et al. |

FOREIGN PATENT DOCUMENTS

| | | | |
|---|---|---|---|
| CN | 1097729 | A | 1/1995 |
| CN | 104193607 | A | 12/2014 |
| CN | 104355977 | A | 2/2015 |
| CN | 104496778 | A | 4/2015 |
| DE | 2145308 | A1 | 3/1973 |
| EP | 0578550 | A1 | 1/1994 |
| EP | 2639295 | A1 | 9/2013 |
| EP | 2875139 | B1 | 11/2019 |
| FR | 1227595 | A | 8/1960 |
| FR | 2221433 | A1 | 10/1974 |
| GB | 2416769 | A | 2/2006 |
| JP | H01242549 | A | 9/1989 |
| WO | 9965853 | A1 | 12/1999 |
| WO | 2008148760 | A2 | 12/2008 |
| WO | 2009077383 | A1 | 6/2009 |
| WO | 2014016146 | A1 | 1/2014 |
| WO | 2014016576 | A1 | 1/2014 |
| WO | 2015071431 | A1 | 5/2015 |

OTHER PUBLICATIONS

Hui et al.; "Highly Chemo- and Regioselective Reaction of Hydroxybenzenes in Acidic Ionic Liquid;" Bullentin of the Korean Chemical Society, KR; vol. 34; No. 9; Sep. 20, 2013; pp. 2594-2596 (3 pages).
Mattioda et al.; "Glyoxylic Acid;" Ullmann's Encyclopedia of Industrial Chemistry; vol. 17; 2012; pp. 89-92 (4 pages).
Jones et al.; "Acetone-Butanol Fermentation Revisited;" Microbiological Reviews; vol. 50; No. 4; Dec. 1986; pp. 484-524 (41 pages).
List et al.; "Proline-Catalyzed Direct Asymmetric Aldol Reactions;" J. Am. CHem. Soc.; vol. 122; No. 10; 2000; pp. 2395-2396 (2 pages).
Guyon et al.; "Synthetic Applications of Hypophosphite Derivatives in Reduction;" Org. Biomol. Chem.; vol. 13; 2015; pp. 7879-7906 (28 pages).
Fuganti et al.; "Product Distribution in the Microbial Biogeneration of Raspberry Ketone from 4-hydoxybenzalacetone;" Journal of Molecular Catalysis B: Enzymatic 4; 1998; pp. 289-293 (5 pages).
Naikwadiet al.; "Gram-Scale Synthesis of Flavoring Ketones in One Pot via Alkylation-Decarboxylation on Benzylic Carbon Using a Commercial Solid Acid Catalyst;" American Chemical Society; vol. 5; 2020; pp. 14291-14296 (6 pages).
International Search Report issued in Application No. PCT/EP2021/083815, mailed on Jan. 18, 2022 (5 pages).
Written Opinion issued in Application No. PCT/EP2021/083815, mailed on Jan. 18, 2022 (6 pages).

*Primary Examiner* — Ana Z Muresan
(74) *Attorney, Agent, or Firm* — Osha Bergman Watanabe & Burton LLP

(57) ABSTRACT

The present invention relates to a process for preparing frambione, comprising a step of condensing phenol and glyoxylic acid.

6 Claims, 1 Drawing Sheet

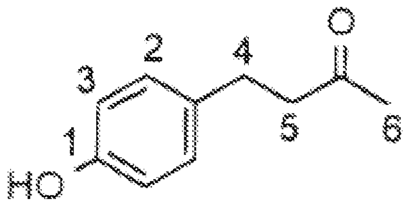

PROCESS FOR PREPARING FRAMBIONE

FIELD OF THE INVENTION

The present invention relates to a process for preparing frambione, comprising a step of condensing phenol and glyoxylic acid.

PRIOR ART

Frambione, or 4-(4-hydroxyphenyl)-2-butanone, is the main aromatic compound in raspberries, but is also present in cranberries or blackberries.

Frambione is used in perfumery, cosmetics or in the agrifood industry to give a fruity odor. This natural aromatic compound may be extracted from fruits at a rate of 1 to 4 mg per kilogram of raspberries. Given the very low abundance of this aromatic compound in the fruit, synthetic processes have been developed, notably:

- by alkylation of phenol in the presence of butenone as described in FR1227595, or in Guo Hui et al. *Bulletin of the Korean Chemical Society,* 2013, 34(9), 2594-2596,
- by condensation of phenol in the presence of 4-hydroxy-2-butanone, as described in US 2011/257439, DE 2145308, CN104355977 or CN104496778. 4-Hydroxy-2-butanone is prepared by condensation of acetone and formaldehyde;
- by condensation of phenol in the presence of 2-acetyl-2-hydroxymethylethyl acetate, as described in FR 2221433. The compound 2-acetyl-2-hydroxymethylethyl acetate is prepared from formaldehyde and ethyl acetoacetate;
- by condensation of phenol with 1,3-dichloro-2-butene, as described in JP01242549; or
- by demethylation, in the presence of hydrobromic acid, of anisylacetone as described in CN104193607.

These processes have drawbacks and notably use compounds whose harmlessness is known: but-2-en-1-one, formaldehyde or hydrobromic acid.

The present invention is directed toward manufacturing frambione via a novel route using non-toxic and less expensive starting materials. Advantageously, the process allows the manufacture of a new compound: natural frambione, the process advantageously using reagents of natural origin. The process advantageously uses milder operating conditions, notably in terms of temperature or pressure, than the processes of the prior art.

BRIEF DESCRIPTION

A first subject of the present invention relates to a process for preparing frambione, comprising a step (a) of condensing phenol and glyoxylic acid.

The present invention also relates to frambione which may be obtained according to the process of the present invention.

The present invention also relates to frambione with a biobased carbon content of greater than or equal to 50% and strictly less than 100%.

The present invention relates to frambione with a $^{13}C$ isotopic deviation of between −27‰ and −15‰, preferably with a biobased carbon content of greater than or equal to 50%.

The present invention also relates to the use of frambione according to the present invention as a flavor or fragrance.

Finally, the present invention relates to a composition comprising frambione according to the present invention.

FIG. 1: Numbering of the frambione positions used to characterize the D/H ratios

DETAILED DESCRIPTION

In the context of the present invention, and unless otherwise indicated, the expression "between . . . and . . . " includes the limits. Unless otherwise indicated, the percentages and ppm are percentages and ppm by mass.

In the context of the present invention, and unless otherwise indicated, the term "ppm" means "parts per million". This unit represents a mass fraction: 1 ppm=1 mg/kg.

In the context of the present invention, the term "biobased origin" refers to a product that is composed, entirely or predominantly, of biological products, or of renewable agricultural (including plant, animal and marine) or forestry materials.

In the context of the present invention, the term "biobased carbon" or "biosourced carbon" refers to carbons of renewable origin such as live agricultural, plant, animal, fungal, microorganism, marine or forestry carbons in a natural environment in equilibrium with the atmosphere. The biobased carbon content is typically assessed by means of carbon-14 dating (also called carbon dating or radiocarbon dating). In addition, in the present invention, the term "biobased carbon content" refers to the mole ratio of biobased carbon to total carbon in the compound or product. The biobased carbon content may preferably be measured via a method of measuring the decay process of $^{14}C$ (carbon-14), in disintegrations per minute per gram of carbon (or 10 dpm/gC), by liquid scintillation counting, preferably in accordance with the standard test method ASTM D6866-16. Said American Standard Test Method ASTM D6866 is considered equivalent to the standard ISO 16620-2. According to said standard ASTM D6866, the test method may preferably use AMS (Accelerator Mass Spectrometry) techniques with $^{13}C$ IRMS (Isotope Ratio Mass Spectrometry) to quantify the biobased content of a given product.

Hydrogen and carbon atoms coexist naturally with their stable isotopes: deuterium and $^{13}C$, respectively. The amount and ratios of D/H and $^{13}C/^{12}C$ are influenced by several factors, notably such as the environment for natural products. The isotopic fingerprint of a product gives information regarding the origin of the product, in particular the natural or fossil origin. The $^{2}H$-SNIF-NMR method measures the deuterium/hydrogen ratio of each site of a molecule. The $^{13}C$-SNIF-NMR method measures the $^{13}C/^{12}C$ ratio of each site of a molecule.

The D/H ratios are measured by comparison to tetramethylurea (TMU), the international reference standard. For example, the measurements may be performed in dioxane or in a dioxane/benzene mixture.

The mean $^{13}C$ isotopic deviation ($\delta^{13}C$) is measured by isotope ratio mass spectrometry (IRMS) relative to PDB (pee bee belemnite), the international reference standard.

Step (a):

The process for preparing frambione comprises a step (a) of condensing phenol and glyoxylic acid and may be represented according to the following scheme:

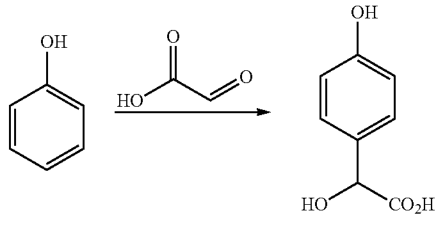

(I)

Step (a) of condensation of phenol and glyoxylic acid allows the formation of 2-hydroxy-2-(4-hydroxyphenyl)acetic acid (Compound I).

Step (a) may be performed according to any process for condensing an aromatic derivative with glyoxylic acid, notably as described in particular in WO 09/077383 or WO 2015/071431.

The phenol may be a biobased phenol or a non-biobased phenol.

According to one embodiment of the present invention, phenol with a biobased carbon content of greater than 50% is also referred to as "biobased phenol". The biobased phenol according to the invention may have a biobased carbon content of greater than 60%, preferably between 75% and 100%, more preferentially between 90% and 100%, more preferentially between 95% and 100%, more preferentially between 98% and 100%, and more preferentially between 99% and 100%. Biobased phenol is a commercial product. It may be obtained naturally from natural resources such as lignin notably via various methods, wood charcoal oil, from plant oil residues or from saccharide. Several biochemical processes are known. Mention may be made, for example, of US 2013/0232852 which describes a process for biorefining lignin biomass. Mention may also be made of EP 2639295 which describes a biochemical process for producing phenol from saccharides.

Given the biobased origin of the phenol, it may contain certain impurities. The nature of the impurities contained in biobased phenol is different from those contained in phenol of fossil origin. Moreover, these impurities may be specific depending on the origin of the phenol and its preparation process. In general, biobased phenol has a purity of greater than or equal to 99%. In general, the content of total impurities in biobased phenol is less than or equal to 1%, and greater than or equal to 0.5%. In general, the content of each impurity in biobased phenol is between and 0.1%, preferably between 0.01% and 0.08%.

In general, biobased phenol has an average $\delta^{13}C$ isotopic deviation of between −33‰ and −20‰, preferably between −30‰ and −25‰, very preferentially between −30‰ and −27‰.

The glyoxylic acid may be a biobased glyoxylic acid or a non-biobased glyoxylic acid.

According to one embodiment of the present invention, the glyoxylic acid with a biobased carbon content of greater than 50% is also referred to as "biobased glyoxylic acid". The biobased glyoxylic acid according to the invention may have a biobased carbon content of greater than 60%, preferably between 75% and 100%, more preferentially between 90% and 100%, more preferentially between 95% and 100%, more preferentially between 98% and 100%, and more preferentially between 99% and 100%. Both biobased and non-biobased glyoxylic acid may be purchased from several producers. Certain processes for producing biobased glyoxylic acid are described in the prior art. In particular, various biochemical processes are available. For example, U.S. Pat. No. 5,219,745 describes an industrially advantageous process for the biochemical production of glyoxylic acid. Alternatively, biobased glyoxylic acid may be produced according to well-known industrial methods (see for example "Glyoxylic Acid" in Ullmann's Encyclopedia of Industrial Chemistry, G. Mattioda and Y. Christidis, Vol. 17 pages 89-92, 2012) from biobased starting materials, such as biobased ethanol, or biobased glycerol or biobased ethylene glycol.

Due to the biobased origin of the glyoxylic acid, it may contain certain impurities. The nature of the impurities contained in biobased glyoxylic acid is different from those contained in glyoxylic acid of fossil origin. Moreover, these impurities may be specific depending on the origin of the glyoxylic acid and its preparation process.

According to a particular aspect, the biobased glyoxylic acid used in the present invention generally has an average $^{13}C$ isotopic deviation of between −33‰ and −7‰, preferably between −31‰ and −9‰, preferentially between −30‰ and −10‰, and very preferentially between −31‰ and −25‰.

According to another particular aspect, the biobased glyoxylic acid used in the context of the present invention generally has an average $^{13}C$ isotopic deviation of between −7‰ and −3‰, preferably between −6‰ and −5‰.

The condensation reaction of phenol with glyoxylic acid allows the synthesis of the corresponding condensation product, which is a para-hydroxymandelic acid. This condensation step may give rise to certain impurities, namely an ortho-hydroxymandelic acid (Compound II) and a dimandelic derivative (Compound III). Other phenol impurities may react during the condensation step.

(II)

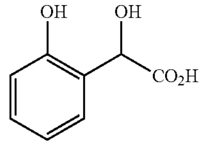

(III)

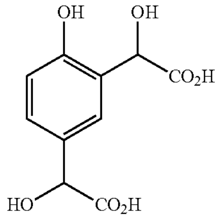

According to one aspect, compound (I) obtained on conclusion of step (a) has a biobased carbon content of greater than or equal to 50%, preferably greater than or equal to 70%, preferentially greater than or equal to 75% and less than or equal to 100%.

The mole ratio between phenol and glyoxylic acid may be between 1.0 and 4.0, preferably between 1.2 and 2.2.

The condensation reaction may be performed in a cascade of stirred reactors. According to one variant, the reaction is performed in a plug flow reactor, optionally comprising a heat exchanger. Such an embodiment is described, for example, in patent application WO 09/077383. The condensation reaction between phenol and glyoxylic acid may be performed in water, in the presence of an alkali metal, said reaction being performed in a plug flow reactor. It may also be performed in a tubular reactor.

Advantageously, the condensation reaction may be catalyzed with a quaternary ammonium hydroxide, according to the reaction described in patent application EP 0 578 550.

According to one embodiment of the invention, the phenol is reacted with the glyoxylic acid in the presence of a base, preferably a mineral base or an organic base, more preferentially an alkali metal, and even more preferentially in the presence of NaOH, KOH, lime or $K_2CO_3$. For economic reasons, sodium hydroxide may be preferred. The alkali metal hydroxide may be used in solution. In this aspect, the alkali metal hydroxide solution may have a concentration of between 10% and 50% by weight. The amount of alkali metal hydroxide introduced into the reaction medium takes into account the amount required to salify the hydroxyl function of phenol and the carboxylic function of glyoxylic acid. According to this variant, the phenol is in the phenoxide form and the condensation product is a mandelate compound. Generally, the amount of alkali metal hydroxide is between 80% and 120% of the stoichiometric amount.

Next, the phenoxide reacts with the glyoxylic acid to form the corresponding para-mandelate. These two reaction steps for preparing glyoxylate and phenoxide may be performed in two separate steps. Alternatively, the glyoxylic acid is placed directly in contact with the phenoxide in the presence of the base.

A possible variant is to perform the reaction in the presence of a dicarboxylic acid catalyst, preferably oxalic acid, as described in international patent application WO 99/65853. The amount of catalyst used, expressed as the ratio of the number of moles of catalyst to the number of moles of glyoxylic acid, may advantageously be chosen between 0.5% and 2.5% and preferably between 1% and 2%.

According to one embodiment of the present invention, the phenol and the alkaline agent are mixed together before the phenol is placed in contact with the glyoxylic acid. Thus, the process according to the invention may include a first step of placing the phenol in contact with an alkali metal hydroxide in aqueous solution, followed by placing the resulting solution in contact with the glyoxylic acid. Advantageously, this embodiment allows for better control of the reaction temperature, since the salification reaction of the glyoxylic acid is exothermic.

According to another embodiment, the process according to the invention comprises in a first step placing the glyoxylic acid in contact with an alkali metal hydroxide in aqueous solution, followed by placing the resulting solution in contact with the phenol.

According to yet another embodiment, the process according to the invention comprises, on the one hand, placing the phenol in contact with the alkaline agent in aqueous solution, and, on the other hand, placing the glyoxylic acid in contact with the alkaline agent in aqueous solution, followed by placing the two resulting solutions in contact.

These optional steps of placing the glyoxylic acid in contact with an alkali metal hydroxide in aqueous solution and/or placing the phenol in contact with the alkaline agent may be performed at a temperature of between 10° C. and 40° C., for example at 15° C. or 35° C.

The reaction mixture obtained may have a viscosity at 20° C. of between 0.5 mPa·s and 50 mPa·s and more preferentially between 1.5 mPa·s and 3 mPa·s. According to the invention, this mixture is introduced into at least one reactor, in which the condensation reaction takes place.

According to another embodiment of the invention, the phenol is reacted with the glyoxylic acid in the absence of any added acidic compound or basic compound. This embodiment is also described in WO 2015/071431.

This condensation step may be performed in an aqueous medium. In the case of use in an aqueous medium, the concentration of the phenol may preferably be between 0.5 and 1.5 mol/liter and more particularly about 1 mol/liter. The glyoxylic acid may be used in aqueous solution with a concentration of, for example, between 15% and 70% by weight. Commercial solutions with a concentration of about 50% by weight are preferably used.

According to another embodiment of the invention, the phenol is reacted with the glyoxylic acid without any solvent, and the glyoxylic acid is glyoxylic acid monohydrate. This embodiment is also described in WO 2015/071431.

According to another embodiment of the invention, the phenol is reacted with the glyoxylic acid in the presence of a catalyst chosen from the group consisting of transition metal complexes containing oxygenated ligands. Said catalyst is preferentially chosen from the group consisting of iron(II) acetate ($Fe(OAc)_2$), iron(III) acetate ($Fe(OAc)_3$), copper(II) acetate ($Cu(OAc)_2$), iron(II) acetylacetonate ($Fe(acac)_2$), iron(III) acetylacetonate ($Fe(acac)_3$), copper(II) acetylacetonate ($Cu(acac)_2$), copper(III) acetylacetonate ($Cu(acac)_3$), and a transition metal complex containing a glyoxylate ligand. This embodiment is also described in WO 2015/071431.

The operating conditions of the reaction may be set according to the reagents and the type of reactor or reactor sequence used.

The reaction temperature may be between 10° C. and 90° C. According to one embodiment, the reaction temperature may be between 10° C. and 20° C. According to another embodiment, the temperature may be between 30° C. and 40° C. Furthermore, the temperature may vary during the course of the reaction. For example, the reaction may be performed at a temperature of between and 20° C. for a period of time, and the temperature may then be raised to between 30° C. and for a finishing phase.

The reaction may be performed at atmospheric pressure, optionally under a controlled atmosphere of inert gases, preferably nitrogen or, optionally, noble gases, in particular argon. Nitrogen is preferentially chosen.

The total residence time of the reagents in continuous operation and the operating or cycle time in batch operation may vary widely, for example from a few minutes to several hours or even several days, notably as a function of the operating conditions, notably as a function of the reaction temperature. When the temperature is between 10° C. and 20° C., the total residence time of the reagents may be between 10 hours and 100 hours. When the temperature is between 30° C. and 50° C., the total residence time of the reagents may be between 30 minutes and 30 hours.

After the condensation reaction, the resulting condensation compound may be separated from the reaction mixture via conventional separation techniques, notably by crystallization or by extraction with a suitable organic solvent. A neutralization step may be performed.

As a variant, the reaction mixture obtained after the condensation reaction may be used in its existing form. However, it is preferable to recover the unreacted phenol. Since phenol is generally in excess relative to the glyoxylic acid, the unreacted phenol fraction is advantageously recovered from a recycle loop, for example by distillation of the water/phenol azeotrope. This excess reduces the likelihood of forming dimandelic acid type compounds (i.e. compounds resulting from the condensation of two glyoxylic acid molecules with one guaiacol molecule). The unreacted phenol may be recovered by acidification, as described in WO 2014/016146. It consists in adding a mineral acid, for example hydrochloric or sulfuric acid, to adjust the pH to between 5 and 7, and then extracting the unreacted phenol in an organic solvent, notably in ether or toluene. After extraction, the aqueous and organic phases may be separated.

Step (b):

The process for preparing frambione may also comprise a step (b) of decarboxylating oxidation of the compound of formula (I) obtained on conclusion of step (a) to form a compound of formula (IV).

Step (b) is a step in which compound (I) is oxidized to form compound (IV) according to the following scheme, and carbon dioxide is released:

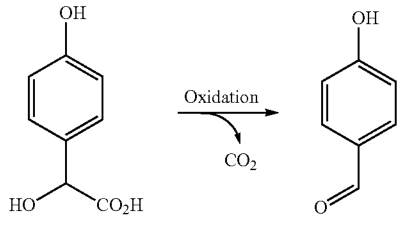

(I) (IV)

Furthermore, compounds (II) and (III) obtained from step (a) may also be oxidized under the same conditions to form compounds (V) and (VI).

(V)

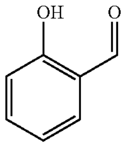

(VI)

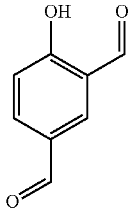

The impurities contained in the biobased phenol that may have reacted in step (a) are also liable to be oxidized under the conditions of step (b).

The oxidation may be performed under an oxidizing atmosphere, such as $O_2$ or in air.

According to one variant, the reaction medium is an aqueous alkaline medium, preferably a mineral base and more preferentially sodium or potassium hydroxide, so as to form the corresponding phenoxide, and to capture the released $CO_2$, in carbonate form.

The reaction may be performed continuously or batchwise, for example in a highly diluted medium in water.

The reaction may be catalyzed. A catalyst for this oxidation reaction may be chosen from catalysts comprising at least one metallic element chosen from the group formed by copper, nickel, cobalt, iron, manganese and any mixture thereof. As examples of inorganic or organic copper compounds, mention may notably be made of cuprous and cupric bromide; cuprous iodide; cuprous and cupric chloride; basic cupric carbonate; cuprous and cupric nitrate; cuprous and cupric sulfate; cuprous sulfite; cuprous and cupric oxide; cupric hydroxide; cuprous and cupric acetate; and cupric trifluoromethylsulfonate. As specific examples of nickel derivatives, mention may be made of nickel(II) halides, such as nickel(II) chloride, bromide or iodide; nickel(II) sulfate; nickel(II) carbonate; nickel(II) hydroxide; salts of organic acids containing from 1 to 18 carbon atoms, notably such as acetate or propionate; nickel(II) complexes, such as nickel (II) acetylacetonate, nickel(II) dichlorobis(triphenylphosphine) or nickel(II) dibromobis(bipyridine); and nickel(0) complexes, such as nickel(0) bis(1,5-cyclooctadiene) or nickel(0) bisdiphenylphosphinoethane. As examples of cobalt-based compounds, mention may notably be made of cobalt(II) and (III) halides, such as cobalt(II) chloride, bromide or iodide or cobalt(III) chloride, bromide or iodide; cobalt(II) and cobalt(III) sulfate; cobalt(II) carbonate, basic cobalt(II) carbonate; cobalt(II) orthophosphate; cobalt(II) nitrate; cobalt(II) and cobalt(III) oxide; cobalt(II) and cobalt (III) hydroxide; salts of organic acids containing from 1 to 18 carbon atoms, notably such as cobalt(II) and cobalt(III) acetate or cobalt(II) propionate; cobalt(II) complexes, such as hexaminecobalt(II) or (III) chloride, hexaminecobalt(II) or (III) sulfate, pentaminecobalt(III) chloride or triethylenediaminecobalt(III) chloride. Use may also be made of iron-based catalytic systems, generally in the form of oxides, hydroxides, or salts, such as iron(II) and iron(III) chloride, bromide, iodide, or fluoride; iron(II) and iron(III) sulfate; iron(II) and iron(III) nitrate; or iron(II) and iron(III) oxide. Use may also be made of iron(II) acetate ($Fe(OAc)_2$), iron(III) acetate ($Fe(OAc)_3$), iron(II) acetylacetonate ($Fe(acac)_2$) or iron(III) acetylacetonate ($Fe(acac)_3$). The reaction may also use manganese-based catalytic systems such as manganese(II) carbonate or manganese(III) acetate. The oxidation reaction may be catalyzed, for example, with a catalytic system comprising two metal elements chosen from the group formed by copper, nickel, cobalt, iron, manganese and any mixture thereof. The teachings of WO 2008/148760 may be applied for the preparation of compound (IV). The present invention notably covers the reactions described according to patent application WO 08/148760.

In a first stage, the condensation compound (IV) obtained on conclusion of step (a) is reacted with the base (preferably sodium hydroxide) so as to salify the phenoxide function of the condensation compound. Next, oxidation in an oxidizing medium (preferably air) produces a compound of formula (IV) and $CO_2$ (trapped as carbonate). At the end of the oxidation reaction, a compound of formula (IV) is obtained in salified form, i.e. with a hydroxyl group in salified (ionic) form, and various impurities, including tars, are obtained. In a subsequent step, the acidification of the compound of formula (IV) in salified form in the reaction medium is performed with a strong acid, for example sulfuric acid.

According to another embodiment of the invention, the oxidation reaction may be performed in the absence of any added acidic or basic compounds. This embodiment is also described in WO 2015/071431.

According to one aspect, compound (IV) obtained on conclusion of step (b) has a biobased carbon content of greater than or equal to 50%, preferably greater than or equal to 70%, preferentially greater than or equal to 75% and less than or equal to 100%.

Step (c):

The process for preparing frambione may comprise a step (c) of condensation of the compound of formula (IV), obtained on conclusion of step (b), with acetone to form a compound of formula (VII).

Step (c) is a condensation of the compound of formula (IV) obtained on conclusion of step (b) with acetone, followed by dehydration, to form a compound of formula (VII).

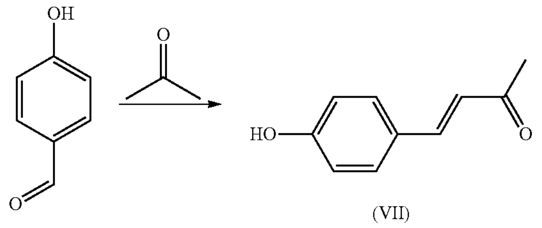

(VII)

(IV)

According to one aspect, the acetone used in step (c) is a biobased acetone. The biobased acetone has a biobased carbon content of between 75% and 100%, more preferentially between 90% and 100%, more preferentially between 95% and 100%, more preferentially between 98% and 100%, and more preferentially between 99% and 100%. Biobased acetone is a commercial product. It may be obtained naturally from natural resources such as by fermentation of sugars from corn residues, notably residues from the sugar industry. Several biochemical processes are known, as described in Jones, D. T. and Woods, D. R. (1986) *Microbiol. Rev.* 50: 484-524, or EP 2875139.

Given the biobased origin of the acetone and its production process, it may contain certain impurities, notably such as methanol, isopropanol or aldehydes. These impurities may be specific depending on the origin of the acetone.

The biobased acetone used in the present invention generally has an average $^{13}C$ isotopic deviation of between −10‰ and −2‰, preferably between −8‰ and −4‰.

The nature of the impurities contained in the biobased acetone is different from those contained in fossil-based acetone. Moreover, these impurities may be specific depending on the origin of the acetone and its preparation process. In general, acetone of biobased origin has a purity of greater than or equal to 99%. In general, the content of total impurities in the biobased acetone is less than or equal to 1%, and greater than or equal to 0.5%. In general, the content of each impurity in the biobased acetone is between 0.005% and 0.1%, preferably between 0.01% and In general, step (c) is performed in the presence of at least 1 equivalent of acetone, preferably not more than 5 equivalents of acetone, for example 2 equivalents of acetone.

Step (c) may be performed in the presence of a base or an acid.

According to a first aspect, step (c) is performed in the presence of a base. According to one particular aspect, the base may be present in a catalytic amount. According to another aspect, step (c) is performed in the presence of 1 equivalent of base. In general, the amount of base is less than or equal to 2 equivalents.

The base used may be a mineral base, such as KOH or NaOH. The base may be in aqueous solution at a concentration of between 10% and 50% by weight, preferably between 15% and 25% by weight.

The base used may also be a basic solid of an alkali metal, alkaline-earth metal, rare-earth metal or transition metal such as oxides, hydroxides, carbonates, or hydrooxycarbonates, preferably chosen from the group consisting of $Li_2O$, $Na_2O$, $Al_2O_3$, $K_2O$, $Cs_2O$, BaO, MgO, $BaCO_3$, $CeO_2$ and $La_2O_3$.

The base used may also be an anion-exchange resin with basic properties.

In general, the reaction is maintained at a temperature of between 10° C. and 60° C., preferably between 20° C. and 50° C., preferentially between 25° C. and 40° C. The reaction is generally performed in a solvent, preferably chosen from water, acetone, alcohols, or mixtures thereof. Preferably, the alcohol is chosen from methanol, ethanol and isopropanol. This embodiment is notably described in CN 1097729.

According to another aspect, step (c) is performed in the presence of an acid. Step (c) may be performed in a mixture comprising water, an alcohol, preferably ethanol, acetone and an acid or with an acid in catalytic amount. According to one aspect, the amount of acid is generally less than or equal to 1 equivalent, relative to the amount of compound of formula (IV), preferably less than or equal to 0.8 equivalent, preferentially less than or equal to 0.5 equivalent. In general, the amount of acid is greater than or equal to 0.01 equivalent, preferably greater than or equal to 0.1 equivalent. The solvent of step (c) may be chosen from water, acetone, alcohols, acetic acid or mixtures thereof. According to another aspect, the reaction is performed in a water/acid mixture; generally, the volume of water relative to the volume of acid is between 1:1 and 5:1. The acid used may also be a cation-exchange resin with acidic properties.

In general, the reaction is maintained at a temperature of between 10° C. and 60° C., preferably between 20° C. and 50° C., preferentially between 25° C. and 40° C. The acid is generally a strong acid, preferably chosen from acids with a pKa of less than or equal to 2, such as sulfuric acid, triflic acid, hydrochloric acid or hydrobromic acid.

According to another aspect, step (c) may be performed in the presence of an amino acid, preferably chosen from proline, azetidine-2-carboxylic acid, piperidine-2-carboxylic acid, 4-hydroxypyrrolidine-2-carboxylic acid, pyrrolidine-2-carboxamide, thiazolidine-4-carboxylic acid and 4-acetoxypyrrolidine-2-carboxylic acid. The amount of amino acid is generally between 15% by volume and 40% by volume. The solvent is generally a mixture of DMSO and acetone. These conditions are notably described in *J. Am. Chem. Soc.* 2000, 122 (10), 2395. However, contrary to what is described in said document, the reaction allows the predominant formation of the α,β-unsaturated ketone.

Advantageously, compound (VII) obtained on conclusion of step (c) has a biobased carbon content of greater than or equal to 50%, preferably greater than or equal to 70%, preferentially greater than or equal to 75% and less than or equal to 100%.

According to a particular aspect, compound (VII) obtained on conclusion of step (c) is recovered in salified form.

Step (d):

The process for preparing frambione may comprise a step (d) of hydrogenation of the compound of formula (VII) obtained on conclusion of step (c), in protonated or salified form.

Step (d) is a hydrogenation step of the compound of formula (VII) obtained on conclusion of step (c) to form frambione (VIII).

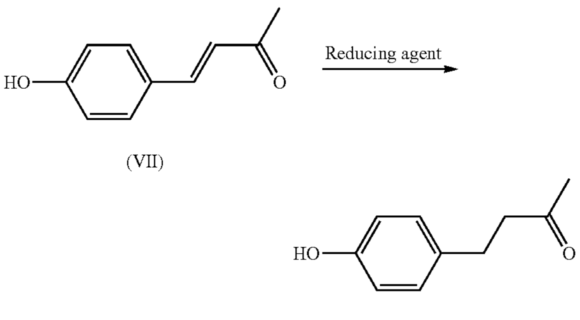

(VII)

(VIII)

According to one aspect of the present invention, step (d) is performed in the presence of a reducing agent with or without heterogeneous catalysis.

Preferably, step (d) is performed in the presence of a metal-based catalyst, preferably chosen from Pd, Pt, Ni, Ru and Rh-based catalysts, such as Pd/C, Pt/alumina or Raney nickel.

The amount of catalyst is generally greater than or equal to 0.1% by weight, preferably greater than or equal to 0.5% by weight, and less than or equal to 25% by weight, preferably less than or equal to 20% by weight.

Step (d) is generally performed in the presence of a reducing agent; in particular, the reducing agent may be chosen from dihydrogen, phosphite and hypophosphite derivatives as described in *Org. Biomol. Chem.*, 2015, 13, 7879-7906. The reducing agent may be chosen from $HCO_2(NH_4)$, $NaH_2PO_2$, $Na_2HPO_3$ and $HCO_2H$.

The amount of reducing agent is generally greater than or equal to 1 equivalent relative to the amount of compound of formula (VII), preferably greater than or equal to 1.5 equivalents, and less than or equal to 10 equivalents, preferably less than or equal to 7 equivalents, very preferentially less than or equal to 5 equivalents.

Generally, the solvent may be chosen from the group consisting of water, alcohols, or acetic acid and mixtures thereof; in particular, the solvent may be water, methanol, ethanol, isopropanol, acetic acid or mixtures thereof.

According to a particular aspect, step (d) may be performed in the presence of a base, preferably a strong base, very preferentially a non-nucleophilic strong base. Preferably, the base may be chosen from tertiary amines, such as triethylamine.

Step (d) is generally performed at a temperature greater than or equal to 25° C., preferably greater than or equal to 30° C., preferentially greater than 40° C., very preferentially greater than 50° C. In general, the temperature of step (d) is less than or equal to 190° C., preferably less than or equal to 175° C., very preferentially less than or equal to 150° C. According to a particular aspect, step (d) is performed at a temperature of between 25° C. and 100° C.

Step (d) may be performed at atmospheric pressure; alternatively, step (d) may be performed under autogenous pressure.

According to another aspect, step (d) may be performed by biochemical transformation; in particular, the transformation of the compound of formula (VII) into frambione of formula (VIII) may be performed by means of a microorganism having ene-reductase activity, as notably described in GB 2416769 or in *Journal of Molecular Catalysis B: Enzymatic* (1998), 4(5-6), 289-293.

According to a particular aspect of the present invention, steps (c) and (d) may be performed without isolation of the compound of formula (VII). Steps (c) and (d) may be performed in a "one-pot" process.

According to another aspect, steps (c) and (d) may be performed without isolation of the compound of formula (VII) and may be performed by heterogeneous catalysis, notably in the presence of a resin, preferably an acidic resin. This embodiment is notably described in *ACS Omega* 2020, 5, 14291-14296.

According to another aspect, steps (c) and (d) may be performed without isolation of the compound of formula (VII) and may be performed by acid catalysis, in the presence of a reducing agent and a metal-based catalyst. Preferably, the metal-based catalyst is chosen from Pd, Pt, Ni, Ru and Rh-based catalysts, such as Pd/C or Raney nickel. The reducing agent is generally chosen from $NaH_2PO_2$, $HCO_2H$ and $NaHPO_2$. The catalyst is generally a strong acid such as hydrochloric acid or sulfuric acid. Generally, the solvent may be chosen from the group consisting of water, alcohols, or acetic acid and mixtures thereof; in particular, the solvent may be water, methanol, ethanol, isopropanol, acetic acid or mixtures thereof.

Advantageously, compound (VIII) obtained on conclusion of step (d) has a biobased carbon content of greater than or equal to 50%, preferably greater than or equal to 70%, preferentially greater than or equal to 75% and less than or equal to 100%.

In a second aspect, the present invention relates to a process for preparing frambione from 4-hydroxybenzyl alcohol and acetone. The preparation process may be represented by the following scheme:

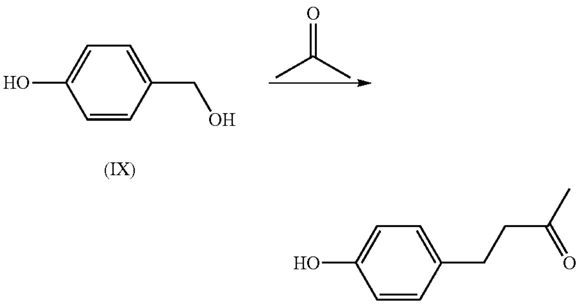

(IX)

(VIII)

4-Hydroxybenzyl alcohol is a commercial product; in particular, the commercial product may be suitable for use in the agrifood industry. The 4-hydroxybenzyl alcohol may be of biobased or non-biobased origin. The 4-hydroxybenzyl alcohol may also be obtained by reduction of the aldehyde (IV) obtained on conclusion of step (b). Advantageously, the 4-hydroxybenzyl alcohol has a biobased carbon content of greater than or equal to 60%, preferably greater than or equal to 70%, preferentially greater than or equal to 75% and less than or equal to 100%.

The acetone may be of biobased origin, as described previously in step (c).

In general, the condensation reaction of the compound of formula (IX) and acetone is performed in a basic medium. The base used may be a base chosen from NaOH, KOH and $K_3PO_4$. The amount of base is generally greater than or equal to 1 equivalent, preferably greater than or equal to 1.1 equivalents, preferentially greater than or equal to 1.5 equivalents relative to the compound of formula (IX). In general, the amount of base is less than or equal to 5 equivalents, preferably less than or equal to 4, very preferentially less than or equal to 3 equivalents relative to the compound of formula (IX).

Preferably, the condensation reaction of the compound of formula (IX) and acetone is performed in the presence of a metal-based catalyst, preferably chosen from Pd, Pt, Ni, Ru and Rh-based catalysts, such as Pd/C or Raney nickel.

The amount of catalyst is generally greater than or equal to 0.1% by weight, preferably greater than or equal to 0.5% by weight, and less than or equal to 25% by weight, preferably less than or equal to 20% by weight.

Generally, the solvent may be chosen from the group consisting of water, alcohols, acetone, dioxane and mixtures thereof; in particular, the solvent may be water, methanol, ethanol, isopropanol, acetone, dioxane or mixtures thereof.

A third aspect of the present invention relates to a frambione that may be obtained according to the process of the invention, in particular to a biobased frambione that may be obtained via the process of the invention.

Advantageously, compound (VIII) obtained on conclusion of the condensation step of the compound of formula (IX) and acetone has a biobased carbon content of greater than or equal to 50%, preferably greater than or equal to 70%, preferentially greater than or equal to 75% and less than or equal to 100%.

A fourth aspect of the present invention covers a frambione with a biobased carbon content of greater than or equal to 50%, preferably greater than or equal to 75% and strictly less than 100%.

The present invention also covers a frambione characterized in that the average $^{13}C$ isotopic deviation is between −27‰ and −15‰, preferably between −23‰ and −15‰, preferentially between −22‰ and −15‰, preferably between −23‰ and −18‰, preferentially between −22‰ and −18‰, very preferentially between −21‰ and −19‰.

In general, the frambione of the present invention has a biobased carbon content of greater than or equal to 50%, preferably greater than or equal to 75%.

In general, the frambione of the present invention has a biobased carbon content of less than or equal to 110%, preferably less than or equal to 105%, preferentially less than or equal to 103%, preferentially less than or equal to 100%, and very preferentially less than strictly 100%.

In the context of the present invention, all the carbon atoms of the frambione according to the present invention are of biobased origin; in particular, the 10 carbon atoms of the frambione of the present invention are of biobased origin. Preferably, 9 carbon atoms of the frambione are of biobased origin; preferably, 8 carbon atoms, preferably 7 carbon atoms, preferably 6 carbon atoms are of biobased origin.

In all the aspects of the present invention, the frambione may have a ratio $(D/H)_3/(D/H)_2$ of less than or equal to 1.10, preferably less than or equal to 1.00, very preferentially less than or equal to 0.90 and very preferentially less than or equal to 0.80.

In all the aspects of the present invention, the frambione may have a ratio $(D/H)_3/(D/H)_2$ of greater than or equal to 0.10, preferably greater than or equal to 0.20, very preferentially greater than or equal to 0.30 and very preferentially greater than or equal to 0.40.

In all the aspects of the present invention, the frambione may have a ratio $(D/H)_5/(D/H)_4$ of less than or equal to 1.10, preferably less than or equal to 1.0, very preferentially less than or equal to and very preferentially less than or equal to 0.85.

In all the aspects of the present invention, the frambione may have a ratio $(D/H)s/(D/H)_4$ of greater than or equal to 0.10, preferably greater than or equal to 0.20, very preferentially greater than or equal to 0.30 and very preferentially greater than or equal to 0.40.

In the context of the present invention, the frambione of the present invention has a ratio $(D/H)_3/(D/H)_2$ of less than or equal to 1.10, preferably less than or equal to 1.00, very preferentially less than or equal to 0.90 and very preferentially less than or equal to 0.80 and a ratio $(D/H)s/(D/H)_4$ of less than or equal to 1.10, preferably less than or equal to 1.0, very preferentially less than or equal to 0.90 and very preferentially less than or equal to 0.85. In general, the frambione has a ratio $(D/H)_3/(D/H)_2$ of greater than or equal to 0.10, preferably greater than or equal to 0.20, very preferentially greater than or equal to 0.30 and very preferentially greater than or equal to 0.40, and a ratio $(D/H)s/(D/H)_4$ of greater than or equal to preferably greater than or equal to 0.20, very preferentially greater than or equal to 0.30 and very preferentially greater than or equal to 0.40.

It is well known to those skilled in the art that the organoleptic properties of a flavoring substance may depend on the presence and amount of certain impurities. This is why the manufacturing process is essential for the taste of the final compound. Advantageously, the frambione of the present invention was found to have satisfactory organoleptic properties. It is noted that the organoleptic profile of the frambione of the present invention is equivalent to the organoleptic profile of frambione extracted from fruits.

According to another aspect, the present invention covers the use of the frambione according to the present invention or the frambione obtained according to the process of the invention as a flavor or fragrance.

Finally, the present invention also covers a composition comprising frambione according to the invention, preferably chosen from the group consisting of food products, beverages, cosmetic formulations, pharmaceutical formulations and fragrances.

EXAMPLES

Example 1

Phenol is condensed with a 50% by weight solution of glyoxylic acid at 30° C. in the presence of NaOH. The compound of formula (I) was obtained in a yield of 60%.

Example 2

After removal of the residual phenol, the compound of formula (I) obtained in Example 1 is oxidized in the presence of a metal catalyst (metal content of 8% by weight) and heated to 75° C. while sparging with air under autogenous pressure (6-8 bar) in an aqueous alkaline medium. The compound of formula (IV) is obtained after acidification with $H_2SO_4$ in a yield of 95%.

Example 3a

The compound of formula (IV) obtained in Example 2 is condensed with acetone (4 equivalents) in acetic acid in the presence of sulfuric acid (0.5 equivalent) at 50° C. The compound of formula (VII) is obtained with a selectivity of 87%.

Example 3b

The compound of formula (IV) obtained in Example 2 is condensed with acetone (8.6 equivalents), in the presence of 10% aqueous sodium hydroxide (2.2 equivalents) at 20° C. The compound of formula (VII) is obtained with a selectivity of 94%.

Example 3c

The compound of formula (IV) obtained in Example 2 is condensed with acetone (4 equivalents), in the presence of glycine (0.3 equivalent) and $NaHCO_3$ (0.1 equivalent) in DMSO at 58° C. The compound of formula (VII) is obtained with a selectivity of 83%.

Example 4a

The compound of formula (VII) obtained in Example 3 is reduced in the presence of $NaH_2PO_2 \cdot H_2O$ (4 equivalents), Pd/C (20% by weight) in a solvent composed of water and ethanol (1:1 mixture). The frambione of formula (VII) is obtained with a selectivity of 81%.

Example 4b

The compound of formula (VII) obtained in Example 3 is reduced in the presence of $Na_2HPO_3 \cdot 5H_2O$ (4 equivalents), Pd/C (20% by weight) in a solvent composed of water and ethanol (1:1 mixture). The frambione of formula (VII) is obtained with a selectivity of 91%.

Example 4c

The compound of formula (VII) obtained in Example 3 is reduced in the presence of $HCO_2H$ (4 equivalents), Pd/C (20% by weight) in a solvent composed of water and ethanol (1:1 mixture). The frambione of formula (VII) is obtained with a selectivity of 78%.

The frambione obtained of formula (VII) has 10 carbon atoms of biobased origin and an isotopic deviation of between −22‰ and −18‰.

The organoleptic profile of the frambione of the present invention is equivalent to the organoleptic profile of frambione extracted from fruits.

The invention claimed is:

1. A process for preparing frambione, comprising the following steps:

step (a): condensing phenol and glyoxylic acid to form a compound of formula (I) according to the following scheme:

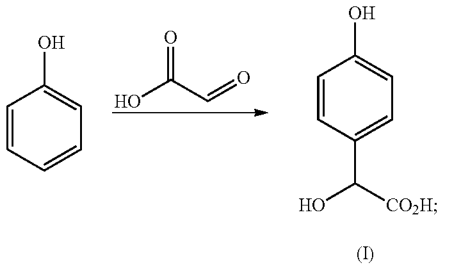

(I)

step (b): oxidizing the compound of formula (I) obtained on conclusion of step (a) to form a compound of formula (IV) according to the following scheme:

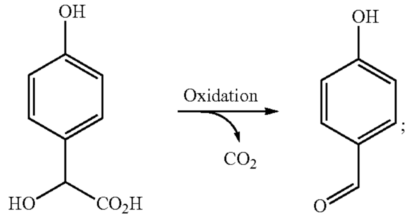

(I) (IV)

step (c): condensing the compound of formula (IV) obtained on conclusion of step (b) with acetone to form a compound of formula (VII) according to the following scheme:

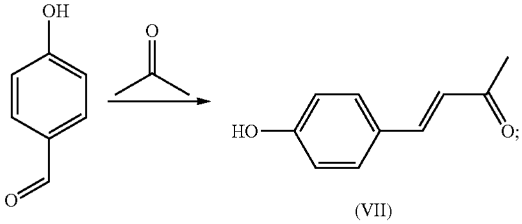

and (VII)

(IV)

step (d): hydrogenating the compound of formula (VII) obtained on conclusion of step (c) to form a compound of formula (VIII) according to the following scheme:

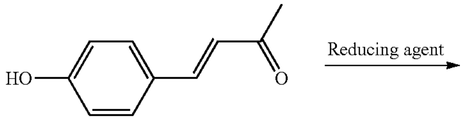

(VII)

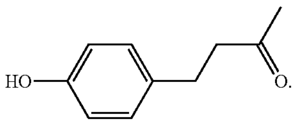

(VIII)

2. The process for preparing frambione as claimed in claim 1, in which at least one compound chosen from phenol and glyoxylic acid is of biobased origin.

3. A process for preparing frambione, comprising a step of condensing 4-hydroxybenzyl alcohol with acetone to form a compound of formula (VIII) according to the following scheme:

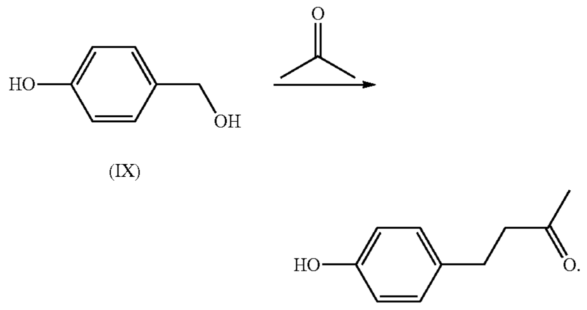

(IX)

(VIII)

4. The process for preparing frambione as claimed in claim 1, in which the acetone is of biobased origin.

5. The process for preparing frambione as claimed in claim 1, further comprising:

wherein step (a) is performed in a solvent, and wherein phenol and glyoxylic acid are present in a mole ratio of between 1.0 and 4.0;

wherein step (b) is performed in a solvent, the same or different from the solvent of step (a), and under an oxidizing atmosphere;

wherein step (c) is performed in a solvent, the same or different from the solvent of step (a) or step (b); and wherein step (d) is performed in a solvent, the same or different from the solvent of step (a), step (b), or step (c), and in the presence of a reducing agent.

6. The process for preparing frambione as claimed in claim 3, wherein condensing 4-hydroxybenzyl alcohol with acetone is performed in a basic medium.

* * * * *